US006650932B1

(12) United States Patent
Menzie et al.

(10) Patent No.: US 6,650,932 B1
(45) Date of Patent: Nov. 18, 2003

(54) MEDICAL TESTING TELEMETRY SYSTEM

(75) Inventors: Wayne Y. Menzie, Arlington, MA (US); John Schafer, North Hampton, NH (US); Keith N. Knapp, II, Townsend, MA (US); Alan M. Cohen, Newton, MA (US)

(73) Assignee: Boston Medical Technologies, Inc., Wakefield, MA (US)

( * ) Notice: Subject to any disclaimer, the term of this patent is extended or adjusted under 35 U.S.C. 154(b) by 0 days.

(21) Appl. No.: 09/570,683

(22) Filed: May 15, 2000

(51) Int. Cl.$^7$ ............................................. A61B 5/0205

(52) U.S. Cl. ........................................ 600/513; 607/25

(58) Field of Search ................................ 600/300, 301, 600/483, 509, 513, 516, 519, 521, 532, 538

(56) References Cited

U.S. PATENT DOCUMENTS 5,299,119 A * 3/1994 Kraf et al. ............. 364/413.06
6,319,200 B1 * 11/2001 Lai et al. .................... 600/300

FOREIGN PATENT DOCUMENTS

EP          0806738 A1    11/1997
WO          WO 99/27842    6/1999

OTHER PUBLICATIONS

International Search Report for PCT/US01/10682.

* cited by examiner

Primary Examiner—Jeffrey R. Jastrzab
Assistant Examiner—Frances P. Oropeza
(74) Attorney, Agent, or Firm—Daly, Crowley & Mofford, LLP

(57) ABSTRACT

A medical testing system includes telemetry features whereby physiological data collected by a collection device at a medical facility is transmitted to a remote processing center for analysis by a trained analyst to provide a test result. In one embodiment, the collection device is a heart rate monitor capable of collecting data with which heart rate variability can be assessed. The heart rate monitor includes a display on which is displayed a waveform showing the breathing performance of the patient during data collection along with standards against which to compare the waveform in order to determine the extent to which the patient followed a predetermined breathing regimen during data collection. The operator of the monitor can use the performance waveform to assess how well the test was taken (i.e., how well the patient complied with the prescribed breathing regimen) and can accept or reject the physiological data accordingly. Also described is a medical testing telemetry system including two processing centers, with each collection device being capable of communicating with both processing centers. Each collection device randomly chooses one of the processing centers for analysis of the collected physiological data. The two processing centers are interconnected in order to permit physiological data and test results to be replicated and stored at both sites.

15 Claims, 10 Drawing Sheets

MEDICAL TESTING TELEMETRY SYSTEM

CROSS-REFERENCE TO RELATED APPLICATIONS

Not applicable.

STATEMENT REGARDING FEDERALLY FUNDED RESEARCH

Not applicable.

BACKGROUND OF THE INVENTION

Heart rate variability has been measured and evaluated to provide an indicator of a patient's autonomic nervous system function. The autonomic nervous system, including the sympathetic and parasympathetic systems, governs involuntary actions of cardiac muscle and certain body tissue. Autonomic neuropathy affects the nerves that serve the heart and internal organs and produces changes in many processes and systems. Autonomic neuropathy is most commonly linked to diabetes; however, several causes are possible, including alcoholism, sleep apnea, and coronary artery disease. Thus, evaluation of the autonomic nervous system function has wide applicability, from diagnosing and treating patients with diabetes to detecting patients at risk for sudden death due to cardiac arrest.

Heart rate variability monitors perform signal analysis on physiological signals, such as ECG signals, in order to measure the interval between certain phenomena, such as the interval between peaks (i.e., R-waves) of the QRS complex, or the R—R interval, to provide an indication of heart rate versus time. Methods and apparatus for accurately detecting R—R intervals are described in U.S. Pat. No. 5,984,954, entitled "Methods and Apparatus for R-Wave Detection."

Various tests have been developed to exercise the autonomic nervous system for purposes of measuring heart rate variability. Two illustrative tests are the Valsalva test and the Expiration/Inspiration (E/I) test, which is sometimes referred to as the metronomic test. The Valsalva test requires that the patient forcibly exhale to a predetermined pressure, such as 40 mmHg, for a predetermined duration, such as 15 seconds, during which the heart rate is monitored. Thereafter, the patient rests for a predetermined duration. The result of the Valsalva test is a ratio of the highest heart rate (as indicated by the shortest R–R interval) during the breathing maneuver to the lowest heart rate (as indicated by the longest R—R interval) during a recovery period after the lo maneuver. In accordance with the E/I test, the patient is instructed to breathe deeply at a frequency of 6 cycles/minute, which has been shown to produce maximal heart rate variability in healthy individuals. The result of the E/I test is a ratio of the average of the heart rate peaks to the average of the heart rate troughs. Several other tests for exercising the autonomic nervous system are used, including the standing test in which the patient's heart rate in both supine and standing positions are compared, and frequency under the power spectrum density curve tests.

Heart rate variability tests are generally performed in a physician's office, at a hospital, or other medical facility. The accuracy of the test results is a function of many factors including the extent to which a patient complies with the particular breathing regimen of the test, the signal processing techniques used to evaluate heart rate variability, and the skill of the medical technician or other operator of the heart rate monitor in administering the test.

SUMMARY OF THE INVENTION

It is an object of the present invention to improve the accuracy of heart rate variability test results.

It is a further object of the invention to facilitate training of medical personnel operating heart rate monitors in order to further improve the accuracy of heart rate variability test results.

These and other objects of the invention are achieved by a heart rate variability system including heart rate monitors for collecting physiological data from patients at a medical facility and a processing center located remotely from, and in communication with the heart rate monitors. The processing center receives the physiological data and analyzes the data to provide test results based on the patient's heart rate variability and indicative of the patient's autonomic nervous system function. The processing center may transmit the results to the heart rate monitor at which the data was collected. In one illustrative embodiment, the analysis performed at the processing center includes use of an automated technique for detecting R—R intervals and also includes intervention by a trained analyst to more accurately identify R—R intervals and anomalies in the resulting heart rate versus time waveform. With this arrangement, the accuracy of the heart rate variability test results is improved due to the use of rigorous automated heart rate variability detection techniques at the processing center and intervention by trained analysts.

Also described is a medical testing system including collection devices for collecting physiological data from patients at a medical facility and a remote processing center for analyzing the physiological data, with each of the collection devices including a display for displaying a waveform showing the patient's performance during collection of the data. Also displayed are performance standards against which to compare the performance waveform in order to determine the extent to which the patient followed a predetermined breathing maneuver during data collection. A user interface of the heart rate monitors is responsive to inputs indicating acceptance of the physiological data if the comparison reveals less than a predetermined deviation between the performance waveform and the performance standards or rejection of the physiological data if the comparison reveals greater than a predetermined deviation. In one embodiment, the test results are compared to predetermined acceptance criteria at the processing center and are rejected if the comparison reveals greater than a predetermined deviation between the results and the predetermined acceptance criteria.

With this arrangement, the accuracy of the test results provided by the processing center is enhanced, since such test results are based only on raw physiological data collected during "well-performed" testing. Stated differently, errors in test results caused by poor test taking are reduced. Thus, because bad physiological data generally will be rejected by the operator of the heart rate monitors and test results falling outside of predetermined acceptance criteria are rejected at the processing center, the accuracy and reproducibility of the tests is improved.

According to a further aspect of the invention, a medical testing system utilizes at least two, redundant processing centers. The system includes at least one collection device in communication with first and second processing centers, each operable to receive physiological data from the collection device, analyze the physiological data to provide a test result, and optionally transmit the test result back to the collection device. In one embodiment, the collection device randomly selects one of the processing centers for receipt of physiological data.

The use of two processing centers advantageously provides analyst availability even in the event of a failure at one of the processing centers or in the communication link to one of the processing centers. Further, use of two processing centers in the medical testing environment of the present invention provides the additional advantage of permitting system changes to be made and extensive, Federally mandated testing to be performed without impacting processing center access, since testing can be performed at one processing center while the other processing center supports collection devices.

The two processing centers are interconnected, preferably by two, redundant communication links. In normal operation, physiological data transmitted to either processing center and test results generated at either processing center are replicated for storage at the other processing center. With this arrangement, since all patient test results are stored at both processing centers, either processing center is capable of providing historical, or trending data to patients and their physicians. Further, in the case of a fault at one of the processing centers relating to its ability to analyze data and generate test results, the unanalyzed physiological data can be analyzed at the other processing center.

BRIEF DESCRIPTION OF THE DRAWINGS

The foregoing features of this invention, as well as the invention itself, may be more fully understood from the following description of the drawings in which.

DETAILED DESCRIPTION OF THE INVENTION

Figure 1:
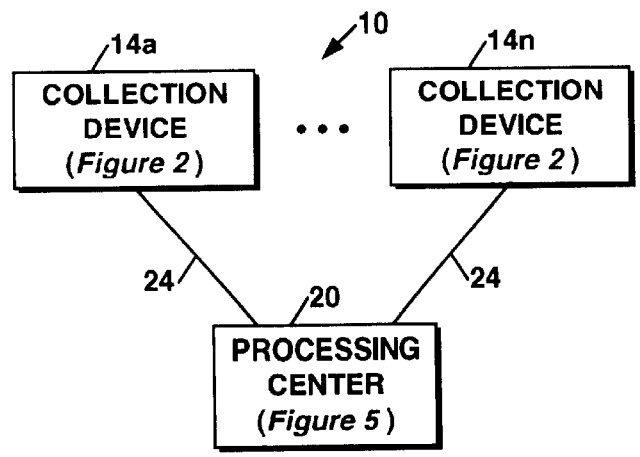
FIG. 1 is a block diagram of a medical testing telemetry system according to the invention.

Referring to FIG. 1, a block diagram of a medical testing telemetry system 10 includes a plurality of collection devices 14a, . . . 14n, each one coupled to a remotely located processing center 20 by a communication link 24. It is contemplated that the collection devices 14a–14n be located at a physician's office, hospital, or other medical facility.

The collection devices 14a–14n are operable to measure physiological signals of a patient which are processed to provide a corresponding test result. The collection devices optionally may perform preliminary, real-time signal processing on the collected data, as will be described further in connection with the illustrative heart rate monitor of FIG. 2. However, it is contemplated that the accuracy and thus, the usefulness of the test results is improved by having a trained analyst located at the processing center 20 analyze the physiological data to provide final test results. The test results may be transmitted by the processing center 20 to the collection device at which the physiological data was collected, as is described below. Alternatively, the test results may remain at the processing center, for example for viewing over a web browser.

Each collection device 14a–14n is coupled to the processing center 20 by a communication connection, or link 24 which includes the public telephone system and may be implemented with various types of hard-wire or wireless media and may further include one or more public or private networks, such as a local area network (LAN) or a wide area network (WAN) which may be part of the Internet. Typical communication links 24 are implemented with Plain Old Telephone Service (POTS) lines or a combination of POTS and voice T1 lines. In one illustrative embodiment, the communication link 24 includes a T1 line comprising 24 digital channels at the 10 processing center 20 and individual POTS lines at each collection device 14a–14n. A telephone company switch coupled between the collection devices 14a–14n and the processing center performs the necessary multiplexing and demultiplexing functions. The communication link 24 may also include a radio frequency (RF) connection which allows the operator of a device 14a–14n to move the device without requiring a hard-wire connection to a telephone line.

Figure 2:
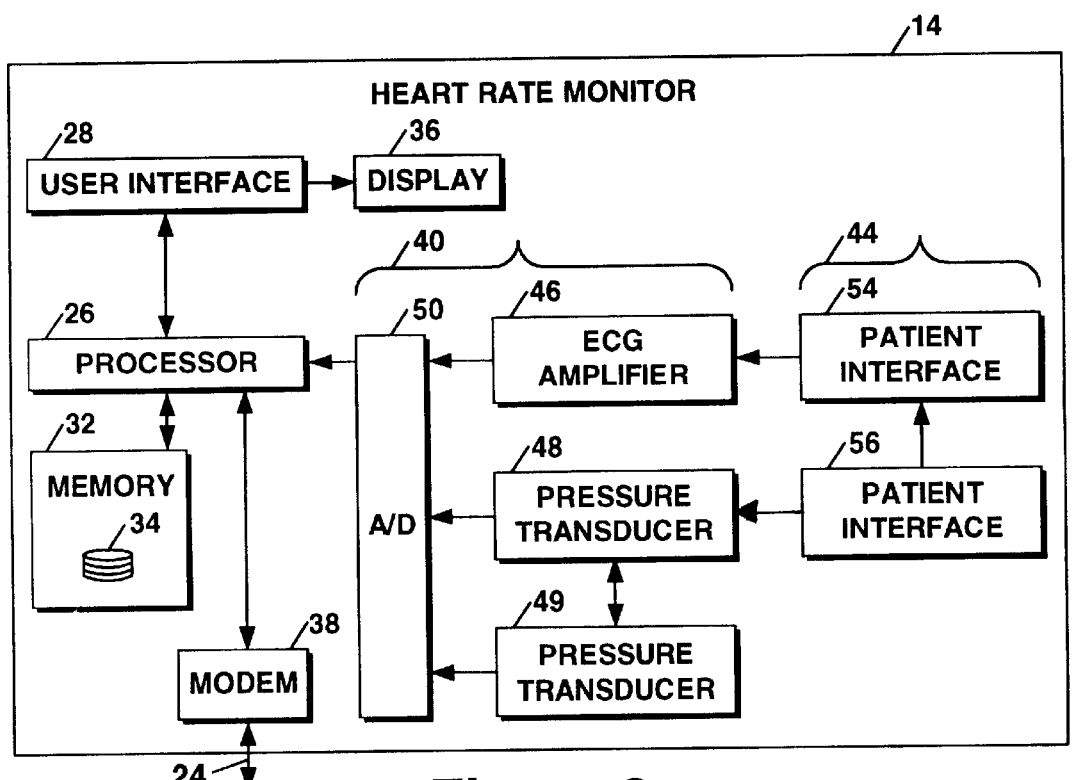
FIG. 2 is a block diagram of an illustrative collection device in the form of a heart rate monitor for use in the system of FIG. 1.

In one illustrative embodiment, each of the collection devices 14a–14n is a heart rate monitor of the type shown in FIG. 2, which is operable to collect physiological data from patients for use in evaluating the patient's heart rate variability and thus, autonomic nervous system function. It will be appreciated by those of ordinary skill in the art that although much of the following description of the telemetry system 10 of FIG. 1 and the alternative telemetry system 130 of FIG. 4 relates to the illustrative heart rate variability application, the apparatus and techniques described herein may be used in connection with other types of medical testing apparatus, such as electrocardiogram machines, x-ray machines, and MRI machines, while still achieving the described advantages.

Referring to FIG. 2, the illustrative heart rate monitor 14 includes a processor 26, a user interface 28, a memory 32, a display 36, data acquisition elements 40, and 30 patient interface elements 44. The processor 26 executes programming instructions by which a patient's heart rate variability is analyzed in real-time in response to the measured physiological data, such as an ECG signal and, optionally, also a blood pressure signal. In the illustrative embodiment, the processor 26 at the collection device performs R-wave detection processing on the patient's ECG signal to generate the heart rate versus time signal for real-time display. The R-wave detection processing performed on the ECG signal to generate the heart rate versus time signal by the processor 26 may be the same as, or different than the R-wave detection processing performed at the processing center 20. In the illustrative embodiment, both the heart rate monitor processor 26 and the processing center 20 implement an R-wave detection scheme of the type described in U.S. Pat.

No. 5,984,954, entitled "Methods and Apparatus for R-Wave Detection," which patent is incorporated herein by reference in its entirety. However, the heart rate versus time data generated at the processing center 20 and used to compute the test results (e.g., the Valsalva and E/I ratios) is the result of a combination of R-wave detection processing techniques and trained analyst intervention.

The processor 26 may take various forms, such as a conventional microprocessor of a standard personal computer, workstation or other microprocessor-driven device. As one example, the processor 26 is an INTEL-compatible microprocessor of an IBM-compatible personal computer running the MICROSOFT WINDOWS graphical user interface. In fact, the heart rate monitor 14 may be implemented using a standard personal computer chassis with certain components (e.g., the data acquisition components 40) provided in the form of circuit modules adapted for insertion into I/O ports of the computer. A modem 38 permits a dial-up connection to be established with the processing center 20 over a POTS line 24.

The memory 32 includes a Random Access Memory (RAM) for temporary data storage and a device with read/write access for permanent data storage, such as a hard drive. A database 34 is provided for storing patient information, test session information, and test results provided by the processing center 20. One illustrative format for the database 34 is described below in conjunction with FIG. 3. In the illustrative embodiment, raw physiological data and test performance data are stored in files external to the database 34.

The user interface 28 may be provided by a number of conventional devices, such as a keyboard, touch screen, and/or mouse. In one illustrative embodiment, the user interface 28 includes a touch screen incorporated into the display 36 and the display is a flat panel LCD display. It will be appreciated by those of ordinary skill in the art that many of the components described herein may be implemented with various hardware and software.

The data acquisition components 40 of the heart rate monitor 14 include an ECG amplifier 46, a first pressure transducer 48 for measuring the pressure at which the patient exhales for use in connection with the Valsalva test and a second pressure transducer 49 for measuring the patient's inspiration flow for use in connection with the Expiration/Inspiration (E/I) test. While the illustrative heart rate monitor 14 is described herein in connection with performing the Valsalva and E/I tests, it will be appreciated by those of ordinary skill in the art that other tests of heart rate variability using the illustrated data acquisition elements 40 may also be performed with the heart rate monitor 14. It will also be appreciated that other physiological signals, such as blood pressure, may be collected by the heart rate monitor 14 by adding corresponding data acquisition and patient interface components and software.

The ECG amplifier 46 operates with a conventional ECG patient interface 54, such as electrode pads adapted for attachment to a patient's chest, and includes signal processing circuitry for conditioning the measured ECG signal for further processing. One suitable commercially available ECG amplifier is of the type sold by Serena Medical Electronics Co., Inc. of San Jose, Calif. under the product name ECG Isolation Amplifier Module Model ECG-170. The output of the ECG amplifier 46 is converted into a digital signal by an analog-to-digital (A/D) converter 50.

The pressure transducer 48 is coupled to a conventional patient interface 56, such as a mouthpiece into which a patient breathes. The pressure transducer 48 measures the pressure differential across a diaphragm within the mouthpiece to provide a pressure transducer output signal indicative of the pressure at which the patient breathes. The pressure transducer output signal is digitized by the A/D converter 50. When the mouthpiece 56 is used in connection with the pressure transducer 49, one end of the mouthpiece is covered. The pressure transducer 49 provides to the A/D converter an output signal indicative of the patient's inspiration flow. The digitized ECG, pressure, and inspiration flow signals are coupled to the processor 26.

According to one aspect of the invention, the pressure and inspiration flow signals which provide breathing performance data are used to evaluate how well a patient performs a particular test. The performance data may also be used to provide feedback to the patient in order to enhance patient compliance with a particular breathing maneuver, as described in a U.S. patent application Ser. No. 08/942,710, entitled "Method and Apparatus for Enhancing Patient Compliance during Inspiration Measurements."

More particularly, a breathing performance waveform illustrating parameters of the patient's breathing during the collection of physiological data for each test is displayed on display 36 to the operator of the monitor 14 in order to permit an assessment to be made as to how well the particular test was performed (i.e., how closely the patient complied with the breathing maneuver associated with the test). Also displayed are standards against which the operator can readily compare the breathing performance waveform. In one embodiment, performance standards are superimposed on the breathing performance waveform in order to facilitate ready comparison of the performance data to the standards. The operator can then accept or reject the raw physiological data as a function of the extent to which the performance data falls within the standards. If, for example, the operator determines that the patient did not closely comply with the specified breathing regimen during data collection, then the raw physiological data can be rejected and new data collected. Alternatively, if the operator determines that the patient closely conformed to the specified breathing regimen, then the raw physiological data is accepted and transmitted to the processing center 20 for analysis.

In one illustrative embodiment, the raw physiological test data is stored in a temporary data file in memory 32 until the operator indicates acceptance or rejection of the test via the user interface 28 based on evaluation of the performance data. If the test is accepted, then the temporary data file is renamed and placed into the collection device database 34, following which the operator can transmit the data to the processing center 20 for analysis and generation of test results. Alternatively, an indication of rejection of the test data causes the temporary data file to be deleted.

With this arrangement, the accuracy of the test results provided by the processing center 20 is enhanced, since such test results are based only on raw physiological data collected during well-performed testing. Stated differently, errors in test results caused from poor test taking are reduced. Thus, because bad physiological data is rejected, the reproducibility of the tests is improved.

Figure 2A:
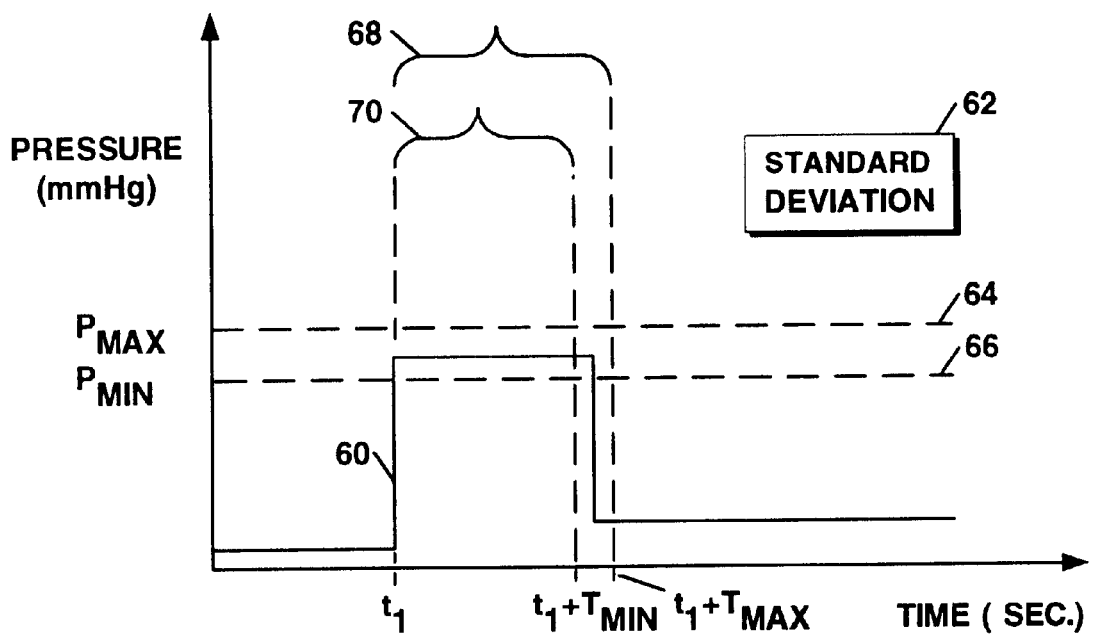
FIG. 2A shows an exemplary breathing performance waveform of pressure versus time for use in connection with the Valsalva test.

Referring also to FIG. 2A, an illustrative patient performance waveform 60 shows pressure versus time during performance of the Valsalva test. Also displayed in the form of a numerical value is a standard deviation 62 which represents the extent to which the patient's breath pressure deviates from the nominal desired 40 mmHg value. The performance standards superimposed on the waveform 60 may include a maximum pressure value Pmax 64, a minimum pressure value Pmin 66, a maximum breath interval Tmax 68, and a minimum breath interval Tmin 70. It will be appreciated by those of ordinary skill in the art that other performance standards may also be displayed.

The operator is provided with guidelines for accepting or rejecting the test data. For example, the operator may be instructed that if the breath pressure remains between Pmax and Pmin for a duration between Tmax and Tmin and the standard deviation is less than a specified percentage, then the test data can be accepted since such conditions indicate that the patient substantially complied with the prescribed breathing maneuver.

Figure 2B:
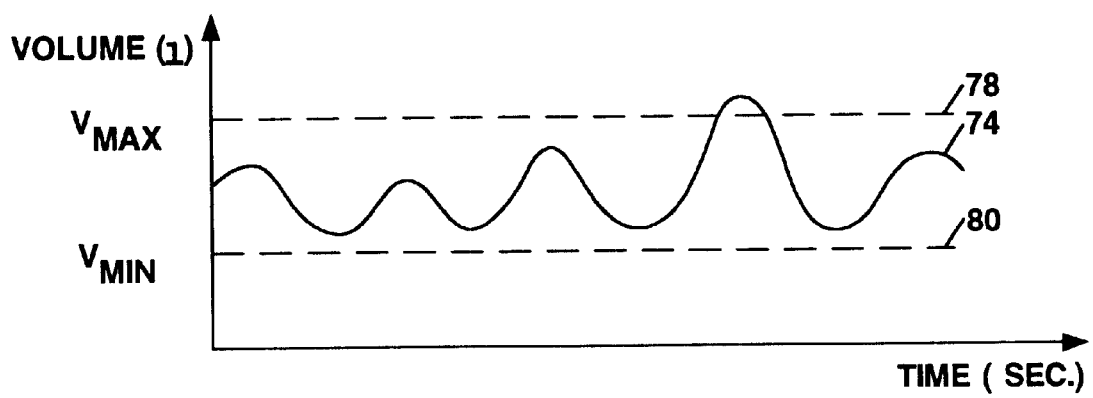
FIG. 2B shows an exemplary breathing performance waveform of volume versus time for use in connection with the E/I test.

Referring to FIG. 2B, in the case of the E/I test, a patient performance waveform 74 shows volume over time, which is provided by integrating the measured inspiration flow signal. Also displayed are standards for use by the operator in assessing the value of the physiological data in the form of a deep breathing maximum value Vmax 78 and a deep breathing minimum value Vmin 80. In the illustrative embodiment, the deep breathing maximum value is set equal to the volume of a reference breath taken by the patient and the deep breathing minimum value is set equal to 60% of the reference volume. In this example, the operator may be instructed that substantial compliance with the desired breathing regimen requires that four of every six breathes fall between the deep breathing maximum value 78 and the deep breathing minimum value 80. It will be appreciated by those of ordinary skill in the art that other measures of test performance, performance standards, formats of presentation, and operator instructions are possible.

Preferably, once raw physiological data is accepted and transmitted to the processing center 20 for analysis, an analyst verifies the operator's decision to accept the physiological data. For this purpose, the test performance data (e.g., breath pressure versus time for the Valsalva test) is transmitted to the processing center along with the raw physiological data. In the illustrative embodiment, the analyst is provided with the same test performance information as the heart rate monitor operator (e.g., waveform 60 of FIG. 2A and waveform 74 of FIG. 2B) for purposes of verifying the accept/reject decision.

According to a further aspect of the invention, an operator of the heart rate monitor 14 can transmit to the processing center 20 test performance data known to be the result of a poorly administered test for the purpose of having a trained analyst study the test performance data and provide consulting advice as to the likely cause of the problem. For example, where an E/I test performance waveform 74 (FIG. 2B) illustrates that the patient is breathing to a volume between 200% and 300% of the reference breath volume, the analyst can infer that the reference breath volume was improperly measured and instruct the operator to re-measure the reference breath volume.

Figure 3:
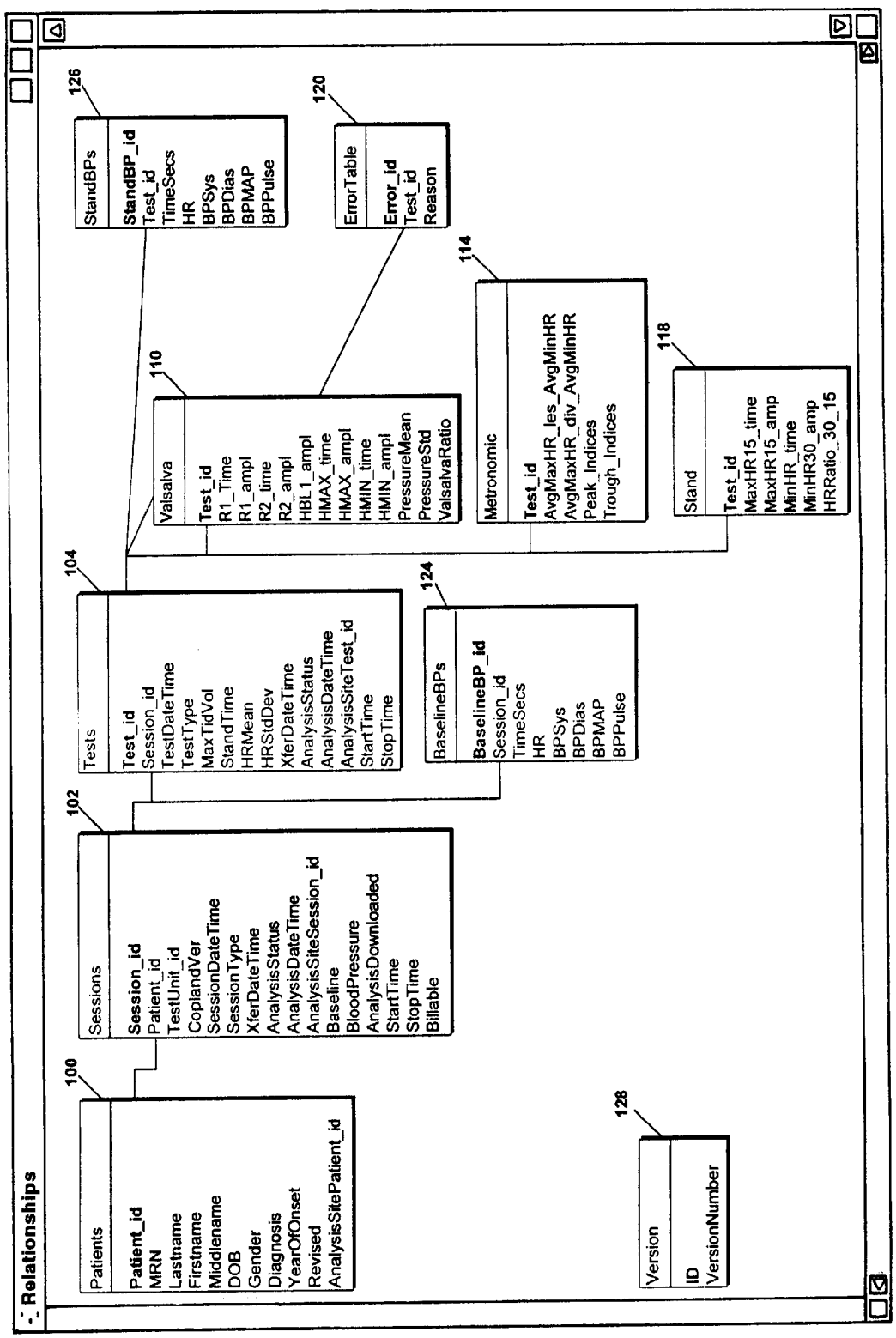
FIG. 3 is shows an illustrative database structure for the heart rate monitor of FIG. 2.

Referring also to FIG. 3, an illustrative format for the collection device database 34 is shown. In the illustrative embodiment, the database 34 is a Microsoft Access 97 database. However, it will be appreciated by those of ordinary skill in the art that various database packages may be used. It will also be appreciated that the database structure shown in FIG. 3, as well as the structure of the database at the processing centers (FIGS. 7A and 7B), is illustrative only and may be readily varied to achieve different database efficiencies and goals.

The database 34 includes a Patients table 100 in which patient demographic information is stored, a Sessions table 102 containing a single entry for each test session, where a test session includes one or more tests performed on a patient at a given time, and a Tests table 104 containing data types common to each of the tests performed in the respective session. Each patient is identified in the Patient's table 100 by a unique identifier (Patient_id) unrelated to the patient's actual identity. Although the entry in the Patient's table 100 for a given patient contains fields for his name, it is the Patient_id that is used throughout the system 10 to identify the patient in order to preserve patient confidentiality. The Sessions table 102 contains information describing the test session, including, but not limited to the Patient_id, the date, the start and stop times of the session, the date that the collected physiological data is transmitted to the processing center 20, whether the data has been analyzed and if so, when analysis occurred. Each entry in the Sessions table 102 has one or more corresponding entries in the Tests table 104 according to how many tests are performed during the given session.

Also provided are tables corresponding to each of the types of tests performed by the heart rate monitor 14 which include, in the illustrative embodiment, a Valsalva table 110, a Metronomic (E/I) table 114 and a Stand table 118. Each entry in the Tests table 104 has a corresponding entry in one of the Valsalva table 110, the Metronomic table 114, and the Stand table 118 once the test results are returned to the collection device.

Following analysis of the raw physiological data by the processing center 20 and transmission of the test results to the heart rate monitor 14, the test results are entered in the appropriate one(s) of the tables 110, 114, 118. For example, the Valsalva ratio (i.e., ValsalvaRatio) is entered in the Valsalva table 110 and the E/I ratio is entered in the Metronomic table 114 (i.e., AvgMaxHR_div_AvgMinHR).

Additional entries in the database 34 following receipt of test results include unique identifiers of the patient, test session, and each analyzed test in the form of an AnalysisSitePatient_id entry in the Patients table 100, an AnalysisSiteSession_id entry in the Sessions table 102, and an AnalysisSiteTest_id entry in the Tests Table 104, respectively. Also entered into the database 34 in response to receipt of a results file is an AnalysisStatus entry in the Sessions table 102 which indicates the status of the test session data as having been analyzed or not, and possible entries in the Error table 120. More particularly, if a particular test is rejected at the processing center, then an identifier of the test (i.e., Test_id) is entered in an Error table 120, along with the reason for rejection.

Optional tables include a BaselineBPs table 124 and a StandBPs table 126, both of which are intended for use with heart rate monitors equipped with a blood pressure acquisition device. In certain cases, it is desirable to measure instantaneous blood pressure with the patient in a supine position and then in a standing position. The two blood pressure measures are compared and evaluated along with heart rate variability in order to diagnose various disorders, such as orthostatic hypotension. Each entry in the Sessions table 102 may have an optional series of entries in the BaselineBPs table 124 that correspond to the baseline blood pressure readings obtained during the Baseline test and an optional series of entries in the StandBPs table 126 that correspond to blood pressure readings obtained while the patient is standing.

In order to support a remote client software update procedure, the collection device database 34 contains a Version table 128 in which the version of the structure of collection device database 34 is stored. The database structure version corresponds to the software version with which it was introduced.

The "results file" which contains test results uploaded from the processing center 20 to the collection device 14 also identifies the most recent version of the client software available (i.e., the software run on the collection devices which is responsible for physiological data acquisition, data transfer to the processing center, signal analysis to provide real-time heart rate versus time data, etc.). Each time a results file is received by a collection device 14, the collection device compares the software version of its executable file with the most recent software version specified in the results file. If the client software versions differ, then the collection device is scheduled to receive a software update. In one illustrative embodiment, the collection device 14 initiates downloading of an update application containing the updated software from the processing center 20 after a predetermined duration. In addition to the latest version of client software, the update application specifies the database structure version required of the collection device database 34 in order to run the updated software. If the update application specifies a database structure different than the database structure version contained in the Version table 128, then the update application also updates the structure of the database 34 and enters the updated database structure version in the Versions table 128.

Figure 4:
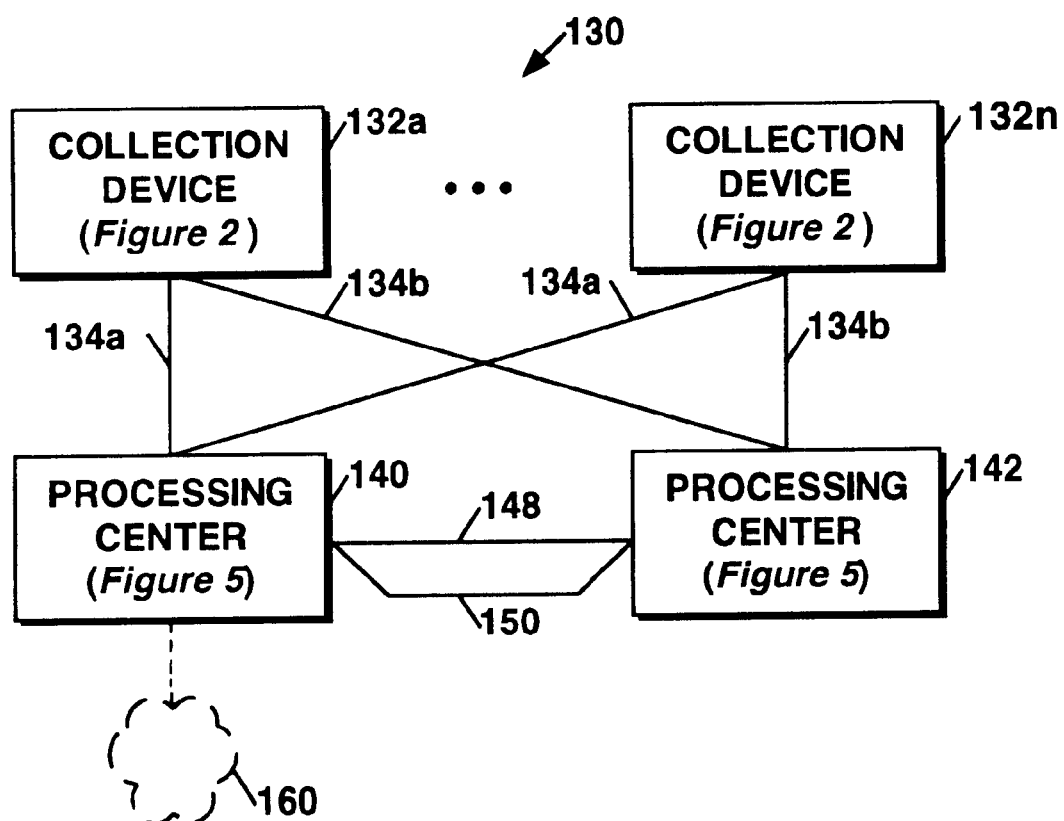
FIG. 4 is a block diagram of an alternative medical testing telemetry system incorporating a processing center redundancy feature of the invention.

Referring also to FIG. 4, an alternative medical testing telemetry system 130 incorporating a processing center redundancy feature of the invention includes a plurality of collection devices 132a–132n and two processing centers 140 and 142. As will become apparent to those of ordinary skill in the art, a minimum of two processing centers 140, 142 is necessary in order to achieve the benefits described below. However, more than two interconnected processing centers may be desirable in certain applications. Illustrative collection devices 132a–132n are heart rate monitors of the type shown in FIG. 2.

Each of the collection devices 132a–132n is capable of communication with the first processing center 140 via a communication link 134a and with the second processing center 142 via communication link 134b. Like the communication links 24 of FIG. 1, links 134a, 134b include the public telephone system and may be implemented with various types of hard-wire or wireless transmission media and may include one or more public or private networks, such as a local area network (LAN) or a wide area network (WAN) which may be part of the Internet. Typical communication links 134a, 134b are implemented with POTS lines or a combination of POTS and voice T1 lines. Thus, each collection device 132a–132n requires configuration of two point to point protocol (PPP) networking configurations in its modem. In one illustrative embodiment, each link 134a, 134b includes a T1 line comprising 24 channels at the processing center 140, 142 which are demultiplexed through the telephone system to provide 24 connections via POTS lines for coupling to collection devices. Preferably, each of the links 134a, 134b is implemented by a different carrier in order to mitigate failures due to equipment trouble or clerical errors.

In a preferred embodiment, each of the collection devices 132a–132n randomly selects one of the processing centers 140, 142 for transmission of physiological data for analysis. For example, where the collection device is a heart rate monitor 14 shown in FIG. 2, the processor 26 of the heart rate monitor executes a routine by which a random one of two possible telephone numbers associated with the two processing centers 140, 142 is dialed by the modem 38. In the event that a dial-up connection cannot be established with the selected processing center, the modem dials the other telephone number. With this arrangement, under normal conditions, the load on the processing centers 140, 142 is shared substantially equally.

Use of two processing centers 140, 142 advantageously provides analyst availability even in the event of a failure at one of the processing centers or in the communication link to one of the processing centers. Further, in the medical testing environment of the present invention, use of two processing centers 140, 142 provides the additional advantage of permitting system changes to be made and extensive, Federally mandated testing to be performed without impacting processing center access. More particularly, improvements are continuously made to the software with which the analysts process physiological data to provide test results and software governing the operation of the processing centers. The Federal Food and Drug Administration (FDA) requires significant testing of any modifications to approved medical systems. With the two-processing center topology of FIG. 4, such improvements can be made as they are developed without the inconvenience of system down time, since the improvements can be tested at one processing center while the collection devices 132a–132n are supported by the other processing center.

The processing centers 140, 142 are interconnected by a pair of redundant communication links 148, 150, as shown. It will be appreciated by those of ordinary skill in the art that the particular choice of communication link type can be varied. As with the links between collection devices and processing centers, the links 148, 150 between the two processing centers can be implemented with various hardwire or wireless transmission media and may include one or more public or private networks. In the illustrative embodiment, one of the links 148 is a data T1 line and the other link 150 is a data ISDN line. Preferably, the two links 148, 150 are of either different types and/or are controlled by different carrier companies, in order to reduce incidences of failed communication between the processing centers.

In normal operation, both the physiological data received at either processing center 140, 142 and test results generated at either processing center 140, 142 are replicated and stored at both processing centers. With this data synchronization arrangement, data backup is achieved. Further, since all patient test results are stored at both processing centers, either processing center is capable of providing historical, or trending data to patients and their physicians, as may be desirable any time tests are performed. For example, every time test results are generated by a processing center and uploaded to a collection device, previous test results of that patient may be uploaded as well. Another advantage of the interconnected processing centers storing replicated data occurs in the case of a fault at one of the processing centers 140, 142 relating to its ability to analyze data and generate test results (e.g., inoperable analyst workstations). In this case, the unanalyzed physiological data can be analyzed at the other processing center.

Additional optional connections to one or more public and/or private networks 160 can be made to one or both of the processing centers 140, 142 in order to enhance features of the medical testing telemetry system 130. As one example, the network 160 may be used to permit customer service personnel to assist operators of the collection devices 132a–132n having difficulty administering tests. In this case, such customer service personnel can be located at a further remote site connected to a processing center through a private network or the Internet. An analyst at one of the processing centers can forward to the customer service representative information regarding poor test performance data and the expected cause (e.g., an inaccurately measured reference breath volume of an E/I test). The customer service representative can then contact the operator and provide instruction to how to improve test performance.

As an another example of a further network connection to one or both of the processing centers, patients and their physicians can be provided with access to test results stored at the processing centers through network 160. Such a network 160 would include the Internet and require strict security features to be implemented in order to preserve patient confidentiality, such as encryption and/or use of a patient ID and password combination.

Figure 5A:
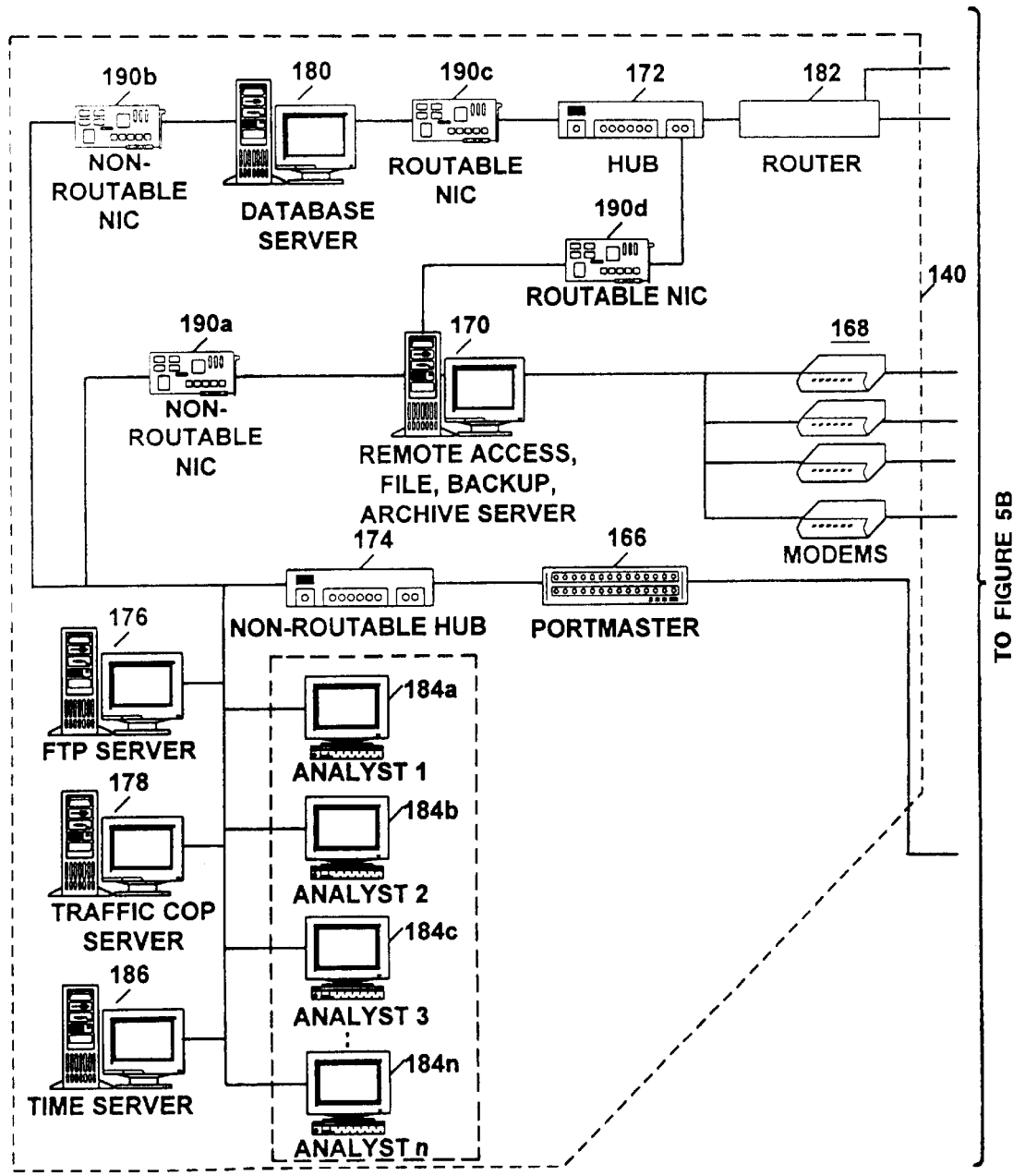
FIGS. 5A and 5B is a more detailed block diagram of the redundant processing centers of FIG. 4.
Figure 5B:
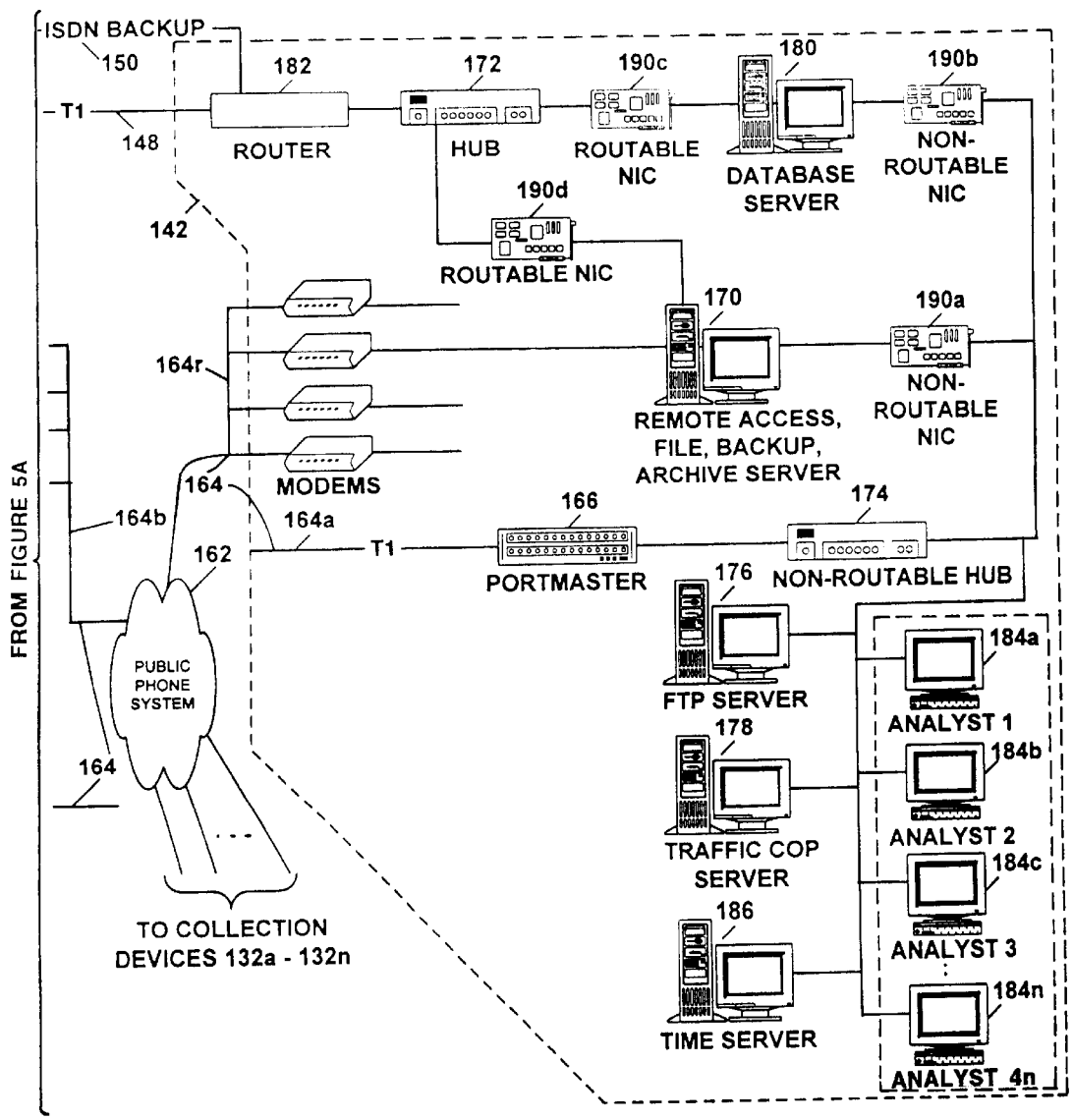

Referring also to FIGS. 5A and 5B, a diagram of illustrative processing centers 140, 142 is shown. The elements of the processing centers are substantially identical, with like reference numbers referring to like elements. Thus, for simplicity, the processing center structure and components will be described in connection with illustrative processing center 140. The structure of the processing centers 140, 142 is also illustrative of the structure of the processing center 20 of FIG. 1, with the exception that the router 182 and communication links 148, 150 between redundant processing centers 140, 142 may be omitted from the processing center 20 of FIG. 1 in which the single processing center 20 supports multiple collection devices 14a–14n.

As noted above, the communication links 134a–134n between a collection device and the processing centers may take various forms. FIGS. 5A and 5B shows two illustrative communication link forms, one labeled 164a and the other labeled 164b. Communication link 164a is provided by a voice T1 line coupled to a Portmaster 166 and communication link 164b is provided by POTS lines coupled to a modem bank 168 which is controlled by a remote access server 170. The Portmaster 166 is available from Lucent Technologies and contains modems used to demultiplex the 24 multiplexed voice lines comprising the T1 line 164a. Use of either or both types of communication links 164a, 164b is suitable for coupling the processing center to a plurality of collection devices through the public phone system 162.

The Portmaster 166 is coupled to a File Transfer Protocol (FTP) server 176 through a non-routable hub 174 (i.e., a hub that has no further connections beyond those shown in FIGS. 5A and 5B). The remote access server 170 is coupled to the FTP server 176 through a non-routable network interface card (NIC) 190a (i.e., a network card which sees no further network connections beyond those shown in FIGS. 5A and 5B). As will be described further in connection with FIG. 6, a compressed data file containing physiological data is transmitted from a collection device to the FTP server 176 for temporary storage prior to analysis. Also, results files containing test results generated at the processing center are placed on the FTP server 176,for downloading to a collection device. In the illustrative embodiment, the processing center 20 implements the TCP/IP protocol on an Ethernet network.

A traffic cop server 178 implements a database management routine by which the FTP server 176 is monitored for unanalyzed physiological data files and the data files on the FTP server 176 are decompressed and placed in a database server 180 through a non-routable NIC 190b to await analysis. The traffic cop application also monitors the database server 180 for analyzed tests so that it can generate results files, compress the results files and place them on the FTP server 170 for downloading by the respective collection device. In the illustrative embodiment, the traffic cop server 178 is implemented on a standard Intel x86 compatible server running Windows NT.

The database server 180 contains the physiological data from the collection devices and, after analysis, the test results generated in response to the physiological data. In the illustrative embodiment, the database server 180 is implemented with Oracle relational database management system (RDBMS) on a Sun Microsystems Ultra server running the Solaris operating system.

A plurality of analyst workstations 184a, 184b, . . . 184n are coupled to the database server 180 and are used by trained analysts to process physiological data and provide test results. The workstations 184a–184n take unanalyzed data from the database server 180 for analysis, as will be described further in connection with FIG. 8. The test results provided by the analysis are packaged by the traffic cop server 178 and placed on the FTP server 176 for downloading by the respective collection device.

In the illustrative embodiment, the remote access server 170 of processing center 140 implements additional functions including that of a file server, archive server and backup server. According to its file server functionality, the server 170 contains the analysis software executed on the analyst workstations 184a–184n, as well as other files shared by processing center components. As a backup server, the server 170 periodically creates a snapshot of the data in the database server 180 and the software files in the file server portion of the server 170 in order to permit restoration of data if software files are lost. Data which is not necessary for long-term use (e.g., raw physiological data received from collection devices) is periodically moved to the archive portion of the server 170. In the illustrative embodiment, only the server 170 at one of the processing centers 140, 142 provides backup functionality since the replication of data at both processing centers 140, 142 would make backup at both processing centers unnecessarily redundant.

As described above, each of the processing centers 140, 142 is coupled to the other with redundant communication links 148, 150, as shown. More particularly, each processing center includes a router 182 for coupling the links 148, 150 to a hub 172 for further coupling to the database server 180 and remote access server 170 through routable NICs 190c, 190d, respectively, as shown. The hub 172 may be coupled to a further network 160 (FIG. 4).

In the illustrative embodiment, one of the links 148 is implemented with a data T1 line and the other link 150 is implemented with a data ISDN line, as shown. The links 148, 150 are provided primarily to permit physiological data and test results to be replicated and stored at both sites periodically (e.g.,.every minute). In the illustrative embodiment, data replication (i.e., synchronization) is achieved using the Advanced Replication feature of Oracle 8i Enterprise Edition referred to as Multimaster Replication running on the traffic cop server. As noted above, preferably the two links 148, 150 are provided by different carriers in order to mitigate failures due to equipment trouble or clerical error.

A time server 186 is provided for maintaining a master clock with which the time clock maintained in the collection devices 132a–132n dialing into the processing center 140 can be synchronized. Use of the time server facilitates process time data collection. For example, the time that it takes the processing center to process physiological data and the collection device to download the test results can be monitored.

Figure 6:
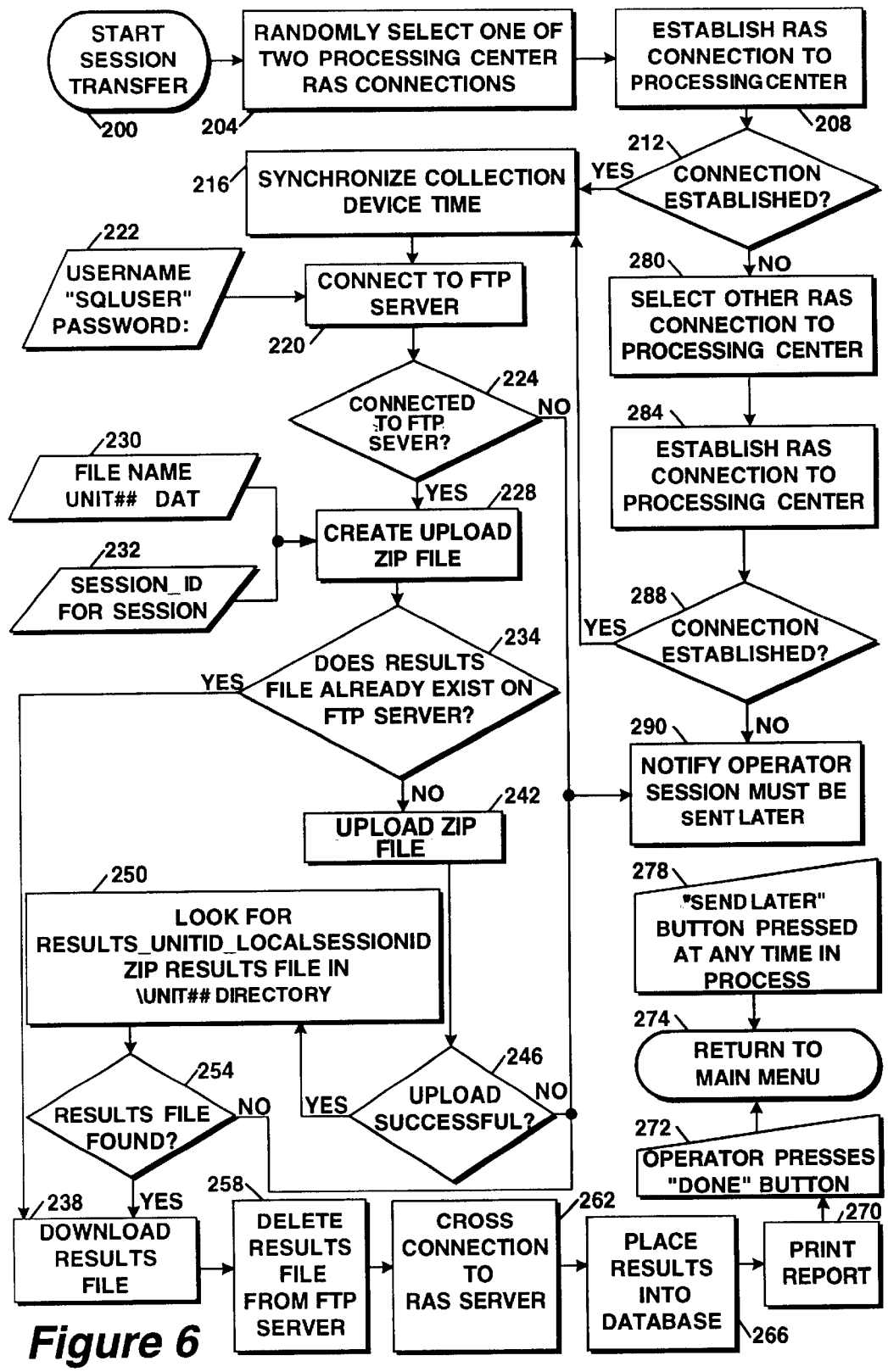
FIG. 6 is a flow diagram illustrating the transfer of raw physiological data from a collection device to a processing center.

Referring also to FIG. 6, a flow diagram shows an illustrative process by which raw physiological data is transmitted from a collection device to a processing center. The flow diagram more specifically illustrates data transmission from a collection device 132a–132n to one of two redundant processing centers 140, 142. However, the process is substantially similar to that implemented by a collection device in communication with only one processing center (FIG. 1), with the exception that steps 204 and 280–288 would be omitted as will become apparent.

The process commences in step 200 with the operator of the collection device providing an input to transmit data, following which the collection device processor 26 (FIG. 2) randomly selects one of the two processing centers 140, 142 for connection in step 204. In step 208, a remote access connection is established by the collection device modem 38 (FIG. 2) to the selected processing center. In step 212, it is determined whether the connection has been established.

If the connection has been established, then the time on the collection device is synchronized to the time maintained by the processing center time server 186 in step 216, following which the collection device is coupled to the FTP server 176 in step 220 in response to input of a valid user name and/or password in step 222. The RAS and FTP connections to the processing center remain open until the physiological data transferred to the processing center is analyzed and returned to the collection device in the form of a results file. In the illustrative embodiment, from the time physiological data transmission begins until the results file is transmitted back to the collection device takes on the order of 5 minutes.

In step 224, it is determined whether a connection to the FTP server 176 has been established. If the connection has not been established, then the operator is notified in step 290 that the session data must be sent to the processing center later. Alternatively, if the connection is established, then a compressed data file is created in step 228 for uploading to the FTP server 176, such as may be created by using industry standard PKZip compatible compression. The Zip file includes patient information from the Patient's table 100 (FIG. 3), with the exception of the patient's name and other patient identifying information, for patient confidentiality purposes. The Zip file further includes session information from the Sessions table 102, test information from the Tests table 104, and performance and physiological data from whatever tests were performed. For example, for the Valsalva test, the Zip file includes the breath pressure data and ECG data. And for the metronomic test, the Zip file contains the breath volume data and the ECG data. The Zip file is also time stamped with the time uploading of the file starts. Creation of the Zip file requires input of the collection device ID (i.e., a unique identifier of the collection device) and a session ID (a unique identifier of the session), as shown at 230 and 232, respectively.

In step 234, it is determined whether a results file having the transmitted collection device ID and session ID already exists on the FTP server 176, as might occur if a connection is lost after physiological data is transmitted to the processing center and before a results file is returned to the collection device. If such a results file exists, then it is downloaded by the collection device in step 238. Alternatively, the Zip file created in step 228 is uploaded to the processing center in step 242 and placed on the FTP server 176.

It is next determined, in step 246, as part of the FTP protocol, whether or not the Zip file was uploaded successfully. If the Zip file was not uploaded successfully, then the operator is notified in step 290 that the session data must be transferred later, as lo shown. Alternatively, the traffic cop server 178 repeatedly looks on the FTP server for a results file corresponding to the uploaded session data in the loop including steps 250, 254, and 246. Once the results file is found in step 254, the results file is downloaded to the collection device in step 238.

Following downloading of the results file to the collection device, the results file is deleted from the FTP server 176 in step 258 and the connection to the remote access server 170 is closed in step 262. In step 266, data from the results file is placed into the collection device database (FIG. 3) and a report is printed at the collection device in step 270. Once the operator presses a "done" button in step 272, the collection device returns to a main menu in step 274. The collection device main menu provides the operator with options to enter patient demographics, view a help system, begin clinical testing, perform system setup procedures, or power off the device. Also, if at any time the operator presses a "send later" button (step 278), the device also returns to the main menu in step 274, as shown.

If, in step 212, a connection was not established to the processing center selected in step 204, then the other processing center is selected in step 280, following which the remote access connection to the newly selected processing center is established in step 284. If it is determined in step 288 that the connection has been established, then step 216 is next performed, as shown. Alternatively, if a connection to the newly selected processing center cannot be established, then the operator is notified, in step 290, that the session data must be sent later.

Figure 7A:
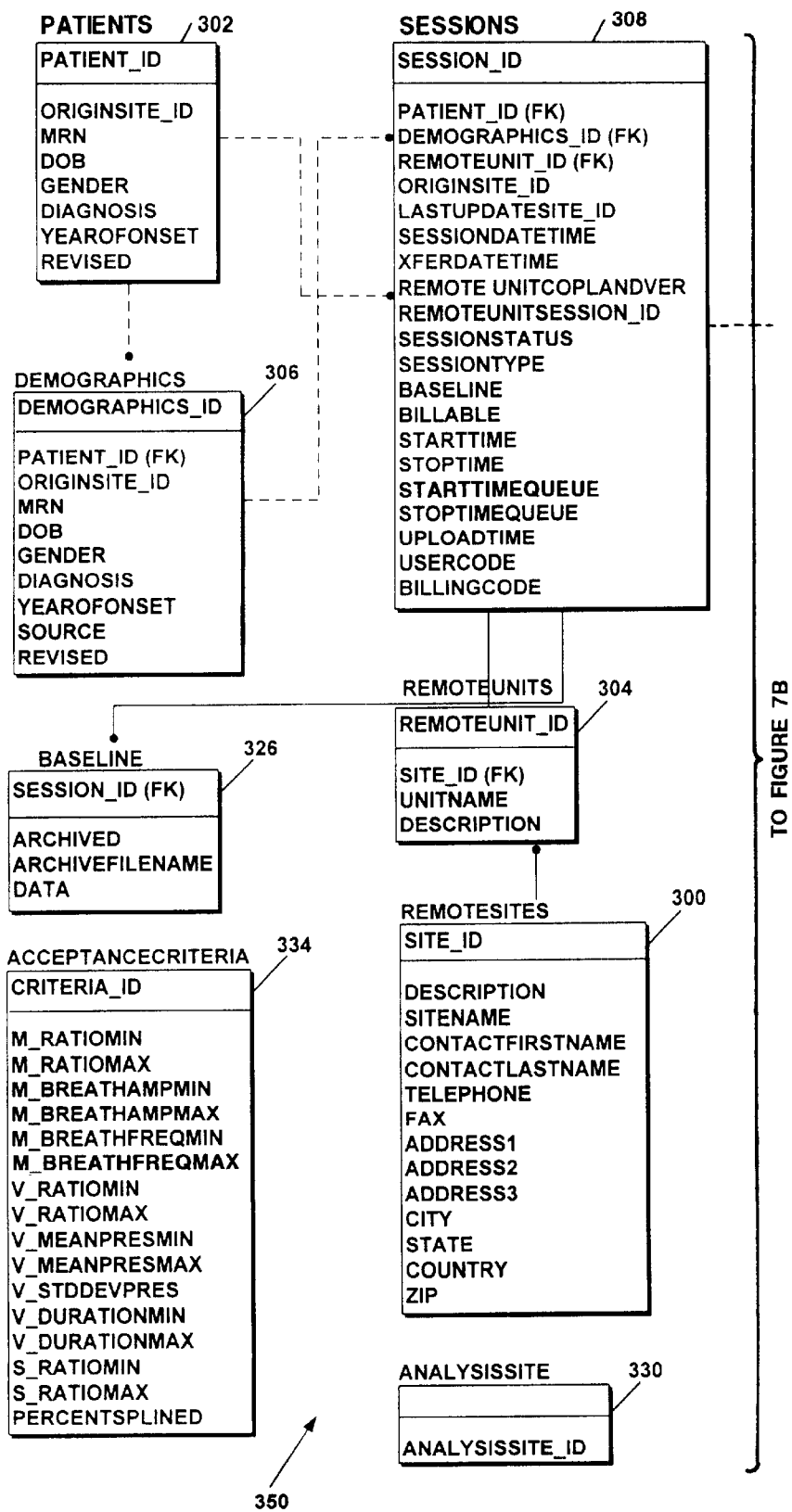
FIGS. 7A and 7B shows an illustrative database structure for the processing centers of FIGS. 5A and 5B.
Figure 7B:
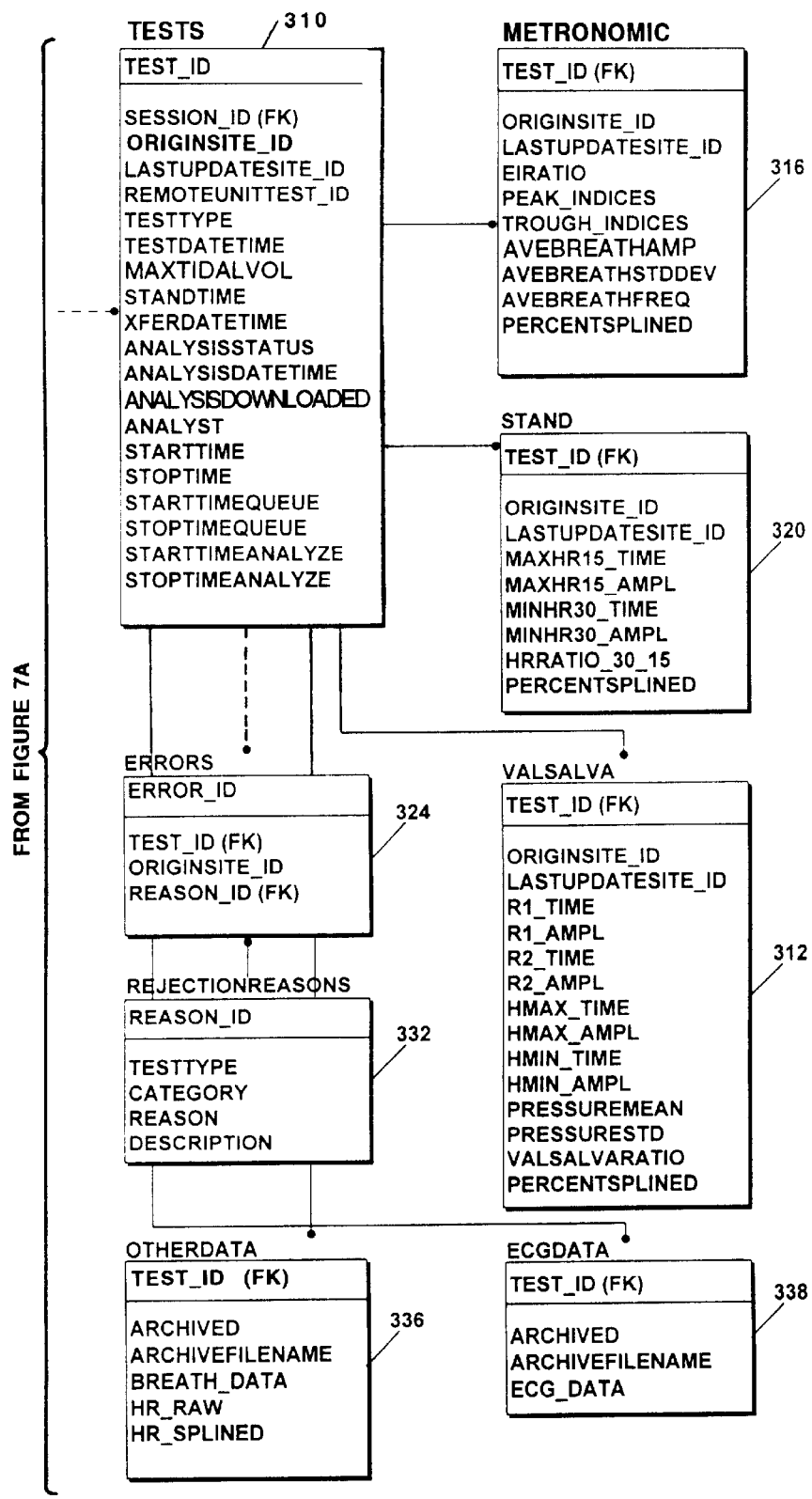

Referring also to FIGS. 7A and 7B, an illustrative format for the processing center database 350 on the database server 180 (FIGS. 5A and 5B) is shown. In the illustrative embodiment, the database 350 is an Oracle 8i enterprise edition. However, it will be appreciated by those of ordinary skill in the art that various database packages may be used. The database 350 includes a Remote Sites table 300 which contains information about the different medical facilities at which collection devices 132a–132n are located, such as facility description, name, contact person, address, etc. For each entry in the Remote Sites table, there may be one or more entries in a Remote Units table 304 for each collection device 132a–132n located at the particular remote site. A collection device, or remote unit is identified, in the illustrative example, by a site ID, a unit name, and a description of the device.

A Patients table 302 contains patient demographic information about each patient for whom data is stored and identifies the patient by the Patient_id only. Patient table entries are processed to provide entries in a Demographics table 306 which is used to collect trending data separate from the individual patient data.

Each entry in the Patients table 302 has one or more entries in a Sessions table 308 depending on how many test sessions, each including one or more tests performed on the patient, were conducted for the particular patient. The Sessions table 308 contains information describing the test session including, but not limited to the Patient_id, the date, the start and stop times of the session, the date that the collected physiological data is transmitted to the processing center, whether the data has been analyzed and if so, when analysis occurred. Each entry in the Sessions table 308 has one or more corresponding entries in a Tests table 310 according to how many tests are performed during the given session. The Tests table 310 contains data types common to each of the tests performed in the respective session.

Also provided are tables corresponding to each of the types of tests performed by the collection devices which include, in the illustrative embodiment, a Valsalva table 312, a Metronomic (E/I) table 316 and a Stand table 320. Each entry in the Tests table 310 has a corresponding entry in one of the Valsalva table 312, the Metronomic table 316, and the Stand table 320 once the test results are returned to the collection device.

Each of the processing center database tables 308, 310, 312, 316, and 320 is substantially identical in content to collection device database tables 102, 104, 110, 114, and 118 of FIG. 3, with the exception that certain processing center tables additionally contain an identifier of the processing center 140, 142 which originally inserted the particular record (originsite_id) and an identifier of the last processing center to update the particular record (lastupdatesite_id). Also, the processing center database 350 contains an Analysis Site table 330 containing an identifier of the processing center at which the database is located (analysissite_id), as shown.

As noted above, since physiological data is replicated and stored at both processing centers 140, 142, either processing center can analyze the data. However, under normal operating conditions, the processing center to which the data was initially transmitted will analyze the data, as will be described further in connection with FIG. 8. Whether a particular processing center initially received the data is determined by comparing the originsite id associated with data awaiting analysis to the analysissite_id. A match between these values indicates that the data was originally sent to the particular processing center.

For diagnostic reasons, it is desirable to be able to track tests for which the data was originally sent to one of the processing centers, but was analyzed at the other processing center. If the originsite_id is different than the lastupdatesite_id, then it can be inferred that the physiological data was originally sent to one processing center, but was analyzed or modified by the other.

An Acceptance Criteria table 334 is provided for storing predetermined test acceptance criteria with which a decision is made by the processing centers 140, 142 as to whether or not to accept or reject particular test results, as is described below in conjunction with FIG. 8. In the illustrative embodiment, the Acceptance Criteria table 334 contains, for the metronomic test, the minimum and maximum E/I ratios, the minimum and maximum average breath amplitudes, and the minimum and maximum average breath frequency. For the Valsalva test, the Acceptance Criteria table 334 contains the minimum and maximum Valsalva ratios, the minimum and maximum average expiration pressures, the maximum standard deviation of expiration pressure, and the minimum and maximum duration of the Valsalva maneuver. For the stand test, the Acceptance Criteria table 334 contains the minimum 30:15 ratio (i.e., the minimum ratio of the highest heart rate within a first duration after standing, such as 15 seconds, to the lowest heart rate within a second duration after standing, such as 30 seconds) and the maximum 30:15 ratio (i.e., the maximum ratio of the highest heart rate within a first duration after standing, such as 15 seconds, to the lowest heart rate within a second duration after standing, such as 30 seconds). The table 334 further contains the maximum percentage of splined heart rate which represents the maximum percentage of the heart rate signal that may be splined.

Raw physiological data in the form of ECG data is stored in an ECG Data table 338 and an Errors table 324, similar to the Error table 120 of FIG. 3, is provided for storing information about rejected tests. A further, Rejection Reasons table 332 includes an entry for each reason for rejecting a test. Finally, the database 350 contains an Other Data table 336 in which test performance data (e.g., breath rate, etc.) is stored. Also provided in the processing center database 350 is an optional Baseline table 326 in which baseline ECG data may be stored (i.e., an ECG signal measured prior to testing). Although not shown in the processing center database 350 of FIGS. 7A and 7B, the processing center database may include tables (similar to tables 124 and 126 of the collection device database) in which blood pressure data is stored in applications in which the heart rate monitors are equipped with a blood pressure acquisition device.

Figure 8:
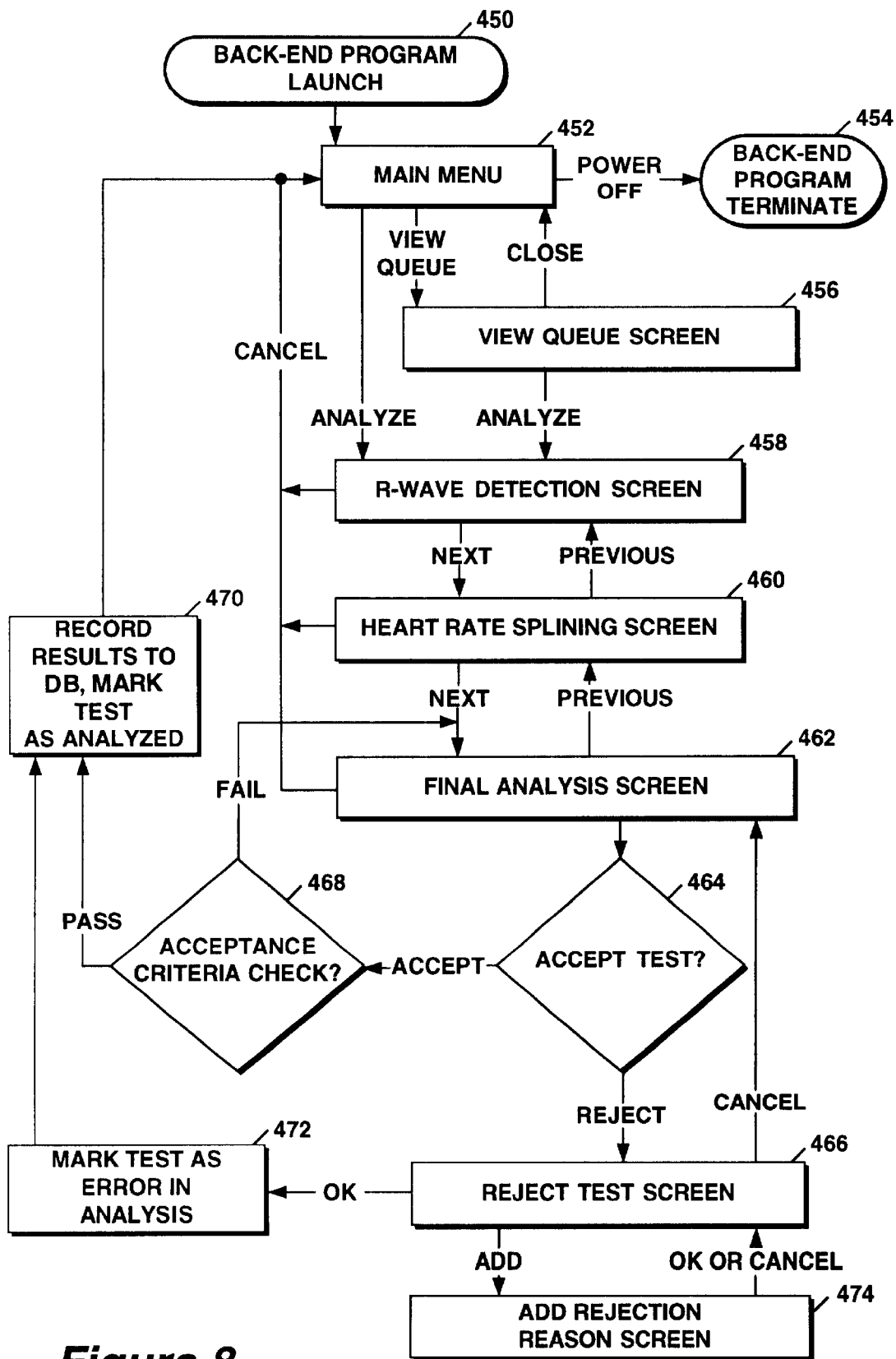
FIG. 8 is a flow diagram illustrating operation of analyst workstations at the processing centers of FIGS. 5A and 5B.

Referring also to FIG. 8, a flow diagram shows an illustrative process by which an analyst at a workstation 184a–184n (FIGS. 5A and 5B) analyzes physiological data and provides corresponding test results. The process of FIG. 8 is implemented by each analyst workstation 184a–184n in each of the redundant processing centers 140, 142 of FIG. 4. However, the process is substantially similar to that which is implemented on an analyst workstation in the single processing center embodiment of FIG. 1, with any exceptions noted below.

The process commences in step 450, following which a main menu is displayed to the analyst in step 452. From the main menu, the analyst can power off the program at step 454, view a "queue screen" in step 456, or analyze test data, beginning at step 458.

The queue screen presents a list containing information about all of the tests currently awaiting analysis. The analyst may use this screen to select a specific test for analysis. In the case where the process of FIG. 8 is implemented on one of redundant processing centers 140, 142, the queue screen may list only those tests intended for analysis at the particular site (i.e., those tests having an originsite_id matching the analysissite_id of the particular processing center). Alternatively, the queue screen may list all unanalyzed tests, with an identifier of the processing center to which the test data was originally sent. Under normal circumstances (i.e., when both processing centers 140, 142 are functional), each processing center analyzes data that is initially transmitted directly to the particular processing center. This arrangement prevents conflicts in which both processing centers analyze the same data. However, if one of the processing centers is down, then all of the tests awaiting analysis can be analyzed at the operational processing center. For example, as described above, if one of the processing centers receives physiological data but is unable to analyze it, then the operational processing center analyzes the received data.

Analysis commences in step 458, either directly from the main menu or from the queue screen. In the illustrative embodiment, in which the collection devices are heart rate monitors used to analyze a patient's heart rate variability, the analysis performed at the processing center involves manipulation of raw ECG data in order to enhance the detection of R-waves and thus, the accuracy of test results which are based on accurate measurement of R—R intervals between R-waves.

The R-wave detection screen displayed to the analyst in step 458 presents a graphical display of the raw ECG data. Superimposed vertical markers indicate R-wave events as detected by a rigorous R-wave detection scheme of the type described in U.S. Pat. No. 5,984,954, entitled "Methods and Apparatus for R-Wave Detection," which patent is incorporated herein by reference in its entirety. The analyst may actuate user inputs to add or remove R-wave detections. For example, some of the displayed R-wave detections may be so close to each other as to suggest that noise, rather than a peak of the QRS complex triggered the detection. In this case, the analyst may delete one or more such detections. Also presented on the R-wave detection screen is a graphical display of heart rate versus time that is updated dynamically as the analyst adds or removes R-wave detections.

Once the analyst has added and removed R-wave detections as necessary, a heart rate splining screen can be displayed in step 460 from which the analyst can modify the heart rate versus time waveform by a technique referred to as splining. Splining is a process by which heart rate variations which are likely to be false based on some criteria are ignored and the heart rate versus time signal is smoothed by bridging the gap across such variations. This screen presents a graphical representation of the heart rate versus time waveform, with a graphical representation of the splined heart rate versus time signal superimposed on it. In the illustrative embodiment, the analyst may vary the following splining parameters: maximum heart rate change, maximum heart rate, and minimum heart rate. The analyst may update, or refresh the graphical representations as parameters are changed.

Once R-wave detections on the ECG signal are edited in step 458 and the heart rate waveform is edited in step 460, a final analysis screen may be viewed in step 462 on which test results and other data are displayed. The final analysis screen is different for each of the autonomic nervous system tests. In the illustrative embodiment, the final analysis screen provides an indication of any test results which do not fall within predetermined acceptable limits (i.e., acceptance criteria) which are stored in the Acceptance Criteria table 334 of the processing center database 350 (FIGS. 7A and 7B). For example, illustrative E/I test limits and Valsalva test limits are between 1.00 and 4.00.

In the case of final analysis for the metronomic test, the screen presents a graphical display of the heart rate versus time, splined heart rate versus time, and inspiration volume data. The extent to which the heart rate data was splined is displayed as a percentage. The analyst is presented with the calculated results of the current test. In one embodiment, a top grid of the results displays the time and amplitude of each heart rate peak and trough used for analysis and a bottom grid displays the E/I Ratio (average of the peak heart rates divided by the average of the trough heart rates), Average Breath Amplitude, Average Breath Standard Deviation and Average Breath Frequency.

In the case of the Valsalva test, the final analysis screen presents the analyst with a graphical representation of the heart rate versus time, splined heart rate versus time and expiration pressure data from the current test. The final analysis screen also presents the analyst with the calculated results of the current test. For example, a top grid of the results displays the start time (r1) of the Valsalva maneuver based on the first expiration above a predetermined level, the stop time (r2) of the Valsalva maneuver based on the last expiration above the predetermined level, the maximum heart rate during the Valsalva maneuver (hmax) and the minimum heart rate during a recovery period following the Valsalva maneuver (hmin). The bottom grid displays the Valsalva Ratio, Duration of Maneuver, Average Pressure and Standard Deviation of Maneuver.

Following the final analysis of step 462, the analyst may attempt to accept or reject the particular test in step 464. If the analyst attempts to accept the test, then it is determined in step 468 whether an acceptance criteria check has been passed. The acceptance criteria check refers to an automated determination of whether the test results fall within predetermined acceptable limits stored in the Acceptance Criteria table 334 of the processing center database 350 of FIGS. 7A and 7B (i.e., the same process which is performed prior to displaying test results from the final analysis screen).

If the test results pass the acceptance criteria test, then the results are placed on the database server 180 (FIGS. 5A and 5B) and the test is marked as analyzed in the analysis queue in step 470, following which the main menu is displayed in step 452, as shown. Alternatively, if the test results do not pass the acceptance criteria test, then the routine displays the final analysis screen again in step 464 with an indication of the invalid results. In particular, the test result values which are outside of the predetermined acceptance limits are highlighted. In this way, if the final analysis screen indicates a rejected test based on non-compliance with the predetermined acceptance limits, the analyst cannot override this determination and accept the test. Thus, the test is rejected in step 464.

Following rejection of a test in step 464 (either by analyst choice or by non-compliance with the predetermined acceptance limits), a reject test screen is displayed in step 466. This screen gives the analyst the option of viewing a rejection reason screen in step 474 for the purpose of documenting the reason for rejecting the test results. In step 472, the rejected test is marked as an error (i.e., placing the rejection reason in the Error table 324 of the processing center database 350 (FIGS. 7A and 7B), following which the main menu is displayed in step 452.

Having described the preferred embodiments of the invention, it will now become apparent to one of ordinary skill in the art that other embodiments incorporating their concepts may be used.

It will be appreciated by those of ordinary skill in the art, for example, that the format of the databases at the heart rate monitors and processing centers are illustrative only and could be readily varied.

Likewise, the software executed at the collection devices for transmitting physiological data to a processing center (FIG. 6) and at the processing centers for analyzing the data to provide test results (FIG. 8) could be varied without departing from the spirit of the invention.

It is felt therefore that these embodiments should not be limited to disclosed embodiments but rather should be limited only by the spirit and scope of the appended claims. All publications and references cited herein are expressly incorporated herein by reference in their entirety.

What is claimed is:

1. A heart rate variability system comprising:
a plurality of heart rate monitors, each located at a medical facility and operable to collect physiological data of a patient from which heart rate variability can be assessed; and
a processing center located remotely from, and in communication with said plurality of heart rate monitors, wherein said processing center is adapted to receive said physiological data from at least one of said plurality of heart rate monitors and to analyze said physiological data to provide results of one or more tests based on the patient's heart rate variability and indicative of the patient's autonomic nervous system function, and wherein said processing center is further adapted to transmit said results to the at least one heart rate monitor at which said physiological data is collected.

2. The heart rate variability system of claim 1 wherein each of said plurality of heart rate monitors is in communication with said processing center through at least one of a POTS line and a T1 line.

3. The heart rate variability system of claim 1 wherein said processing center includes:
   a processor on which an R-wave detection routine is implemented; and
   a user interface adapted to receive an input from an analyst by which R-wave detections are added or deleted.

4. The heart rate variability system of claim 3 wherein said user interface is further adapted to receive an input from said analyst by which a heart rate variability waveform generated in response to said detected R-waves is modified.

5. The heart rate variability system of claim 1 wherein each of said heart rate monitors comprises a display for displaying a waveform showing the breathing performance of said patient during collection of said physiological data and standards against which to compare said waveform in order to determine the extent to which said patient followed a predetermined breathing regimen during collection of said physiological data.

6. The heart rate variability system of claim 5 wherein each of said plurality of heart rate monitors includes a user interface adapted to receive an input from an operator by which said physiological data of said patient is accepted or rejected, wherein only accepted physiological data is transmitted to said processing center for analysis.

7. The heart rate variability system of claim 6 wherein said physiological data of said patient is rejected by said operator if comparison of said waveform to said standards reveals greater than a predetermined deviation between said waveform and said standards.

8. The heart rate variability system of claim 6 wherein said physiological data of said patient is accepted by said operator if (a) comparison of said waveform to said standards reveals less than a predetermined deviation between said waveform and said standards; or (b) comparison of said waveform to said standards reveals greater than a predetermined deviation between said waveform and said standards and said acceptance is based on a request by said operator for feedback from said processing center.

9. The heart rate variability system of claim 1 wherein said processing center is further adapted to compare said results to predetermined acceptance criteria and to reject said results if said comparison reveals greater than a predetermined deviation between said results and said predetermined acceptance criteria.

10. The heart rate variability system of claim 1 wherein said processing center is further adapted to receive input from an analyst in order to provide results of one or more tests based on the patient's heart rate variability and indicative of the patient's autonomic nervous system function.

11. A heart rate variability system comprising:
   a plurality of heart rate monitors, each located at a, medical facility and operable to collect physiological data of a patient from which heart rate variability can be assessed, wherein each of said heart rate monitors comprises a display for displaying a waveform showing the breathing performance of said patient during collection of said physiological data and standards against which to compare said waveform in order to determine the extent to which said patient followed a predetermined breathing regimen during collection of said physiological data; and
   a processing center located remotely from, and in communication with said plurality of heart rate monitors, wherein said processing center is adapted to receive said physiological data from each of said plurality of heart rate monitors and to analyze said physiological data to provide results of one or more tests based on the patient's heart rate variability and indicative of the patient's autonomic nervous system function.

12. The heart rate variability system of claim 11 wherein each of said plurality of heart rate monitors includes a user interface adapted to receive an input from an operator by which said physiological data of said patient is accepted or rejected, wherein only accepted physiological data is transmitted to said processing center for analysis.

13. The heart rate variability system of claim 12 wherein said physiological data of said patient is rejected by said operator if comparison of said waveform to said standards reveals greater than a predetermined deviation between said waveform and said standards.

14. The heart rate variability system of claim 12 wherein said physiological data of said patient is accepted by said operator if (a) comparison of said waveform to said standards reveals less than a predetermined deviation between said waveform and said standards; or (b) comparison of said waveform to said standards reveals greater than a predetermined deviation between said waveform and said standards and said acceptance is based on a request by said operator for feedback from said processing center.

15. A heart rate variability system comprising:
   a plurality of heart rate monitors, each located at a medical facility and operable to collect physiological data of a patient from which heart rate variability can be assessed; and
   a processing center located remotely from, and in communication with said plurality of heart rate monitors, wherein said processing center is adapted to receive said physiological data from each of said plurality of heart rate monitors and to analyze said physiological data to provide results of one or more tests based on the patient's heart rate variability and indicative of the patient's autonomic nervous system function, wherein said processing center is further adapted to compare said results to predetermined acceptance criteria and to reject said results if said comparison reveals greater than a predetermined deviation between said results and said predetermined acceptance criteria.

* * * * *